(12) United States Patent
Petrukhin

(10) Patent No.: US 11,000,492 B2
(45) Date of Patent: May 11, 2021

(54) FLUORENONE COMPOUND FOR THE TREATMENT OF GOUT

(71) Applicant: Konstantin Petrukhin, New Windsor, NY (US)

(72) Inventor: Konstantin Petrukhin, New Windsor, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 410 days.

(21) Appl. No.: 15/774,487

(22) PCT Filed: Nov. 11, 2016

(86) PCT No.: PCT/US2016/061534
§ 371 (c)(1),
(2) Date: May 8, 2018

(87) PCT Pub. No.: WO2017/083652
PCT Pub. Date: May 18, 2017

(65) Prior Publication Data
US 2020/0246289 A1      Aug. 6, 2020

Related U.S. Application Data

(60) Provisional application No. 62/254,922, filed on Nov. 13, 2015.

(51) Int. Cl.
*A61K 31/192* (2006.01)
*A61P 19/06* (2006.01)
*A61K 45/06* (2006.01)

(52) U.S. Cl.
CPC ............ *A61K 31/192* (2013.01); *A61P 19/06* (2018.01); *A61K 45/06* (2013.01)

(58) Field of Classification Search
CPC .... A61K 31/192; A61K 45/06; A61K 31/426; A61K 31/519; A61P 19/06; A61P 19/04; A61P 19/02
See application file for complete search history.

(56) References Cited

U.S. PATENT DOCUMENTS

2011/0014176 A1    1/2011    O'Neil et al.
2013/0189246 A1    7/2013    Petrukhin

OTHER PUBLICATIONS

Pubchem, Substance Record for SID 103424473 Create Date: Dec. 22, 2010. Retrieved from the Internet on Apr. 26, 2018: <https://pubchem.ncbi.nlm.nih.gov/substance/103424473>.
International Search Report dated Jan. 12, 2017 by the international searching authority in connection with PCT International Application No. PCT/US2016/061534.
Written Opinion of the International Searching Authority dated Jan. 12, 2017 in connection with PCT International Application No. PCT/US2016/061534.

*Primary Examiner* — Sarah Pihonak
*Assistant Examiner* — Jason Deck
(74) *Attorney, Agent, or Firm* — John P. White; Gary J. Gershik

(57) ABSTRACT

The present invention provides a method for treating or preventing gout in a subject afflicted therewith comprising administering a compound presented or an ester or salt thereof, so as to thereby treat or prevent the gout in the subject.

20 Claims, 1 Drawing Sheet

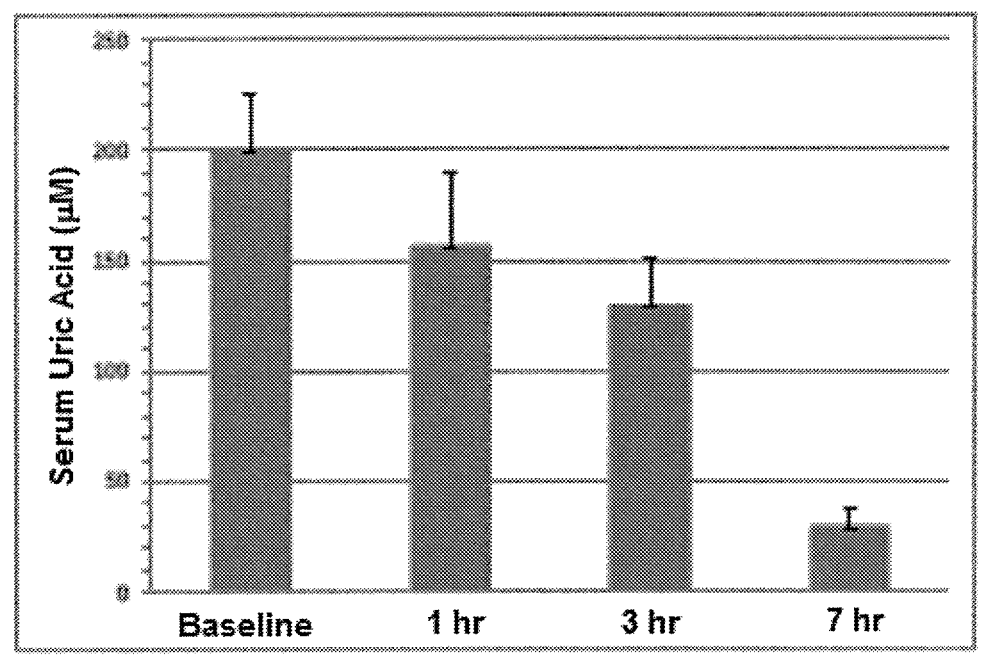

FLUORENONE COMPOUND FOR THE TREATMENT OF GOUT

This application is a § 371 national stage of PCT International Application No. PCT/US2016/061534, filed Nov. 11, 2016, claiming the benefit of U.S. Provisional Application No. 62/254,922, filed Nov. 13, 2015, the contents of each of which are hereby incorporated by reference into the application.

Throughout this application, certain publications are referenced in parenthesis. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Gouty arthritis is the most common form of inflammatory arthritis and affects more than 8 million people in the Unites States (Lawrence, R. C. et al. 2008). Uric acid is a metabolic product resulting from the metabolism of purines, which are found in many foods and in human tissue (Terkeltaub, R. A. 2001; Burns, C. et al. 2013). Gout is caused by excess uric acid levels in the blood, which lead to the deposition of monosodium urate crystals in tissue. These crystals are formed when concentration of uric acid in tissues and in circulation exceeds the solubility limit, leading to gout flares. Risk factors for gout include being overweight or obese, having hypertension, alcohol intake, diuretic use, a diet rich in meat and seafood, and poor kidney function (Choi, H. K. et al. 2004a; Choi, H. K. 2004b; Krishnan, E. 2012).

Acute flares occur when urate crystals in the joint causes acute inflammation. A flare is characterized by pain, redness, swelling, and warmth lasting days to weeks. Pain may be mild or excruciating. Most initial attacks occur in lower extremities. The typical presentation in the metatarsophalageal joint of the great toe (podagra) is the presenting joint for 50% of people with gout. Chronic gout is characterized by chronic arthritis, with soreness and aching of joints. People with gout may also get tophi or lumps of urate crystals deposited in soft tissue. Clinically inactive (intercritical) segments between gout flares occur after an acute flare has subsided. The person with gout continues to have hyperuricemia, which results in continued deposition of urate crystals in tissues and resulting damage. Intercritical segments become shorter as the disease progresses.

Uric acid is synthesized from its precursor, xanthine, by the enzyme called xanthine oxidase (XO). Accordingly, XO inhibitors (e.g., allopurinol and febuxostat) dominate the market (Stamp, L. K. et al. 2015; Love, B. L. et al. 2010). However, elevated levels of circulating uric acid most commonly result from undersecretion of uric acid in the kidneys. With the exception of the marginally effective probenecid, there are no approved treatments that would increase the renal secretion of uric acid.

The incidence and prevalence of gout is rising. This is due to factors such as an increase in the aged population, many of whom take thiazide diuretics and prophylactic aspirin that promote hyperuricemia and lifestyle factors characterized by diets that include excessive fructose and alcohol intake, physical inactivity and abdominal fat accumulation which favor hyperuricemia (Burns, C. et al. 2013; Choi, H. K. et al. 2004a)

Significant unmet clinical need remains in the treatment of gout. Of the 8 million of patients with gout, over 3 million are on urate-lowering therapy (mainly XO inhibitors). Despite this fact, 1 million patients continue to experience 3 or more flares per year indicating the need for better urate-lowering therapy.

SUMMARY OF THE INVENTION

The present invention provides a method for treating or preventing gout in a subject afflicted therewith comprising administering a compound having the structure:

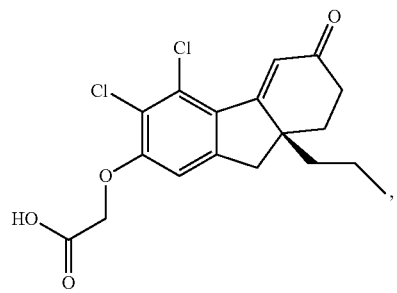 [SMILES: CCC[C@]12CCC(=O)C=C1c1c(cc(OCC(=O)O)c(Cl)c1Cl)C2]

or an ester or salt thereof, so as to thereby treat or prevent the gout in the subject.

BRIEF DESCRIPTION OF THE FIGURES

FIG. 1: Systemic administration of 20 mg of DPOFA intraperitoneally to guinea pigs induced pronounced reduction in the serum uric acid level.

DETAILED DESCRIPTION OF THE INVENTION

The present invention provides a method for treating or preventing gout in a subject afflicted therewith comprising administering a compound having the structure:

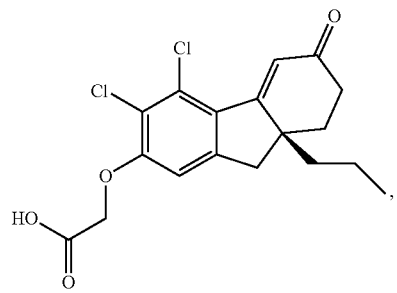 [SMILES: CCC[C@]12CCC(=O)C=C1c1c(cc(OCC(=O)O)c(Cl)c1Cl)C2]

or an ester or salt thereof, so as to thereby treat or prevent the gout in the subject.

The present invention also provides a method for treating or preventing hyperuricemia in a subject afflicted therewith comprising administering a compound having the structure:

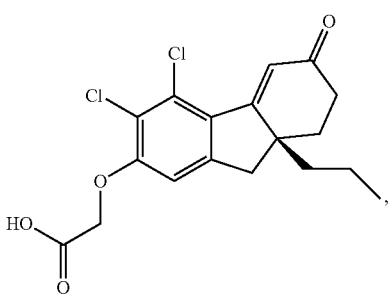 [SMILES: CCC[C@]12CCC(=O)C=C1c1c(cc(OCC(=O)O)c(Cl)c1Cl)C2]

or an ester or salt thereof, so as to thereby treat or prevent the hyperuricemia in the subject.

In some embodiments, the compound treats gout in the subject.

In some embodiments, the compound hyperuricemia gout in the subject.

In some embodiments, the treating comprises increasing uric acid levels in the urine of the subject.

In some embodiments, the treating comprises reducing uric acid levels in the blood of the subject.

In some embodiments, the treating comprises increasing uric acid clearance in the subject.

In some embodiments, the treating comprises decreasing uric acid reabsorption in the kidneys of the subject.

In some embodiments, the treating comprises increasing renal clearance of uric acid in the subject.

In some embodiments, the treating comprises reducing one or more symptoms associated with gout in the subject.

In some embodiments, the treating comprises reducing one or more symptoms associated with hyperuricemia in the subject.

In some embodiments, the one or more symptoms associated with gout are joint pain, joint inflammation, joint redness, decreased range of motion at the joint.

In some embodiments, the one or more symptoms associated with hyperuricemia are gout, joint pain, joint inflammation, joint redness, decreased range of motion at the joint.

In some embodiments, the one or more symptoms associated with hyperuricemia are gout.

In some embodiments, the compound prevents gout in the subject.

In some embodiments, the compound prevents hyperuricemia in the subject.

In some embodiments, the preventing comprises increasing uric acid levels in the urine of the subject.

In some embodiments, the preventing comprises reducing uric acid levels in the blood of the subject.

In some embodiments, the preventing comprises increasing uric acid clearance in the subject.

In some embodiments, the preventing comprises decreasing uric acid reabsorption in the kidneys of the subject.

In some embodiments, the preventing comprises increasing renal clearance of uric acid in the subject.

In some embodiments, the preventing comprises reducing one or more symptoms associated with gout in the subject.

In some embodiments, the one or more symptoms associated with gout are joint pain, joint inflammation, joint redness, decreased range of motion at the joint.

In some embodiments, the one or more symptoms associated with hyperuricemia are gout, joint pain, joint inflammation, joint redness, decreased range of motion at the joint.

In some embodiments, the one or more symptoms associated with hyperuricemia are gout.

In some embodiments, the gout is acute gout.

In some embodiments, the gout is chronic gout.

In some embodiments, acute gout is prevented.

In some embodiments, a recurrence of chronic gout is prevented.

In some embodiments, any of the above methods further comprising administering to the subject a xanthine oxidase inhibitor.

In some embodiments, the xanthine oxidase inhibitor is allopurinol or febuxostat.

In some embodiments, the subject is a mammal.

In some embodiments, the subject is a human.

The present invention also provides a method of lowering uric acid serum levels in a subject comprising administering a compound having the structure:

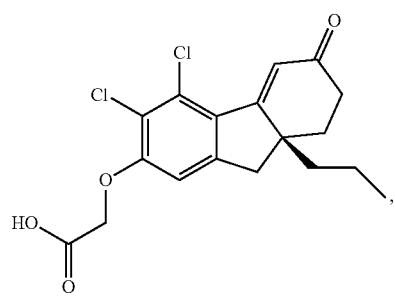 [SMILES: CCC[C@]12CCC(=O)C=C1c1c(cc(OCC(=O)O)c(Cl)c1Cl)C2]

or an ester or salt thereof, so as to thereby lower uric acid serum levels in the subject.

In some embodiments, the treating comprises reducing blood uric acid levels in the subject to less than 7 mg/dL.

In some embodiments, the treating comprises reducing blood uric acid levels in the subject to less than 6 mg/dL.

In some embodiments, the treating comprises reducing blood uric acid levels in the subject to less than 5 mg/dL.

In some embodiments, the subject has blood uric acid level above 7 mg/dL and administration of the compound reduces the uric acid level to below 7 mg/dL.

In some embodiments, the subject has blood uric acid level above 7 mg/dL and administration of the compound reduces the uric acid level to below 6 mg/dL.

In some embodiments, the subject has blood uric acid level above 7 mg/dL and administration of the compound reduces the uric acid level to below 5 mg/dL.

In some embodiments, the subject has blood uric acid level above 7 mg/dL and administration of the compound reduces the uric acid level to normal uric acid levels of 2.4-6.0 mg/dL (female) or 3.4-7.0 mg/dL (male).

In some embodiments, the xanthine oxidase inhibitor, is from the group consisting of allopurinol, febuxostat, oxypurinol, tisopurine, inositol, phytic acid, myo-inositiol, kaempferol, myricetin, and quercetin.

In one embodiment, the use of the compound having the structure:

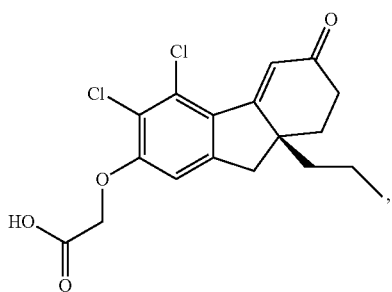 [SMILES: CCC[C@]12CCC(=O)C=C1c1c(cc(OCC(=O)O)c(Cl)c1Cl)C2]

or an ester or salt thereof, for the treatment of gout or hyperuricemia.

In one embodiment, the use of the compound having the structure:

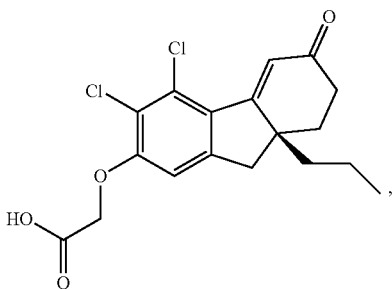 [SMILES: CCC[C@]12CCC(=O)C=C1c1c(cc(OCC(=O)O)c(Cl)c1Cl)C2]

or an ester or salt thereof, for the prevention of gout or hyperuricemia.

The use of the compound the compound having the structure:

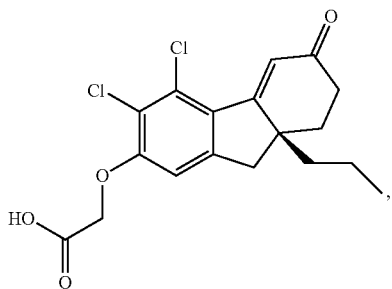 [SMILES: CCC[C@]12CCC(=O)C=C1c1c(cc(OCC(=O)O)c(Cl)c1Cl)C2]

or an ester or salt thereof, for the preparation of a medicament for the treatment of gout or hyperuricemia.

The use of the compound the compound having the structure:

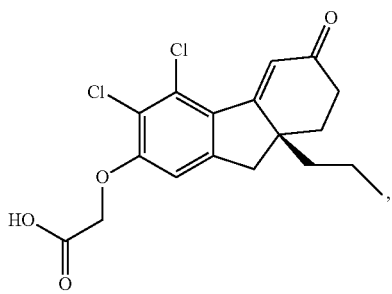 [SMILES: CCC[C@]12CCC(=O)C=C1c1c(cc(OCC(=O)O)c(Cl)c1Cl)C2]

or an ester or salt thereof, for the preparation of a medicament for the prevention of gout or hyperuricemia.

As used herein, the description "pharmaceutically active" is used to characterize a substance, compound, or composition suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department of Health and Human Services, 30$^{th}$ edition, 2010), which are hereby incorporated by reference.

Another aspect of the invention comprises a compound used in the method of the present invention as a pharmaceutical composition.

The compounds used in the method of the present invention may be in a salt form. As used herein, a "salt" is a salt of the instant compound which has been modified by making acid or base salts of the compounds. In the case of the use of the compounds for treatment of gout or hyperuricemia, the salt is pharmaceutically acceptable. Examples of pharmaceutically acceptable salts include, but are not limited to, mineral or organic acid salts of basic residues such as amines. The term "pharmaceutically acceptable salt" in this respect, refers to the relatively non-toxic, inorganic and organic base addition salts of the compounds. These salts can be prepared in situ during the final isolation and purification of the compounds, or by separately reacting purified compounds in their free acid form with a suitable organic or inorganic base, and isolating the salt thus formed.

As used herein, "treating" means slowing, stopping, or preventing the progression of a disease. An embodiment of "treating gout" is delaying or preventing the onset, progression, or mitigating severity of the gout.

The compounds used in the method of the present invention may be administered in various forms, including those detailed herein. The treatment with the compound may be a component of a combination therapy or an adjunct therapy, i.e. the mammal in need of the drug is treated or given another drug for the disease in conjunction with the compounds used in the method of the present invention. This combination therapy can be sequential therapy where the mammal is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the mammal. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of the compound and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise the compound alone, or mixtures of the compound with additional compounds used to treat gout. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the eye, all using dosage forms well known to those of ordinary skill in the pharmaceutical arts.

The compounds used in the method of the present invention can be administered in a mixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier.

This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxy-ethylasparta-midephenol, or polyethyleneoxide-polylysine substituted with palmitoyl residues. Furthermore, the compounds used in the method of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The compounds used in the method of the present invention can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the compounds used in the method of the present invention and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the compounds used in the method of the present invention may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds used in the method of the present invention and compositions thereof of the invention can be coated onto stents for temporary or permanent implantation into the cardiovascular system of a subject.

The compounds and compositions of the present invention are useful for the prevention and treatment of gout.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

The compounds used in the method of the present invention may be prepared by techniques well know in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

Each embodiment disclosed herein is contemplated as being applicable to each of the other disclosed embodiments. Thus, all combinations of the various elements described herein are within the scope of the invention.

This invention will be better understood by reference to the Examples which follow, but those skilled in the art will readily appreciate that the specific experiments detailed are only illustrative of the invention as described more fully in the claims which follow thereafter.

Example 1. DPOFA

The chemical structure of DPOFA is shown below. A non-GMP batch of DPOFA was synthesized by GVK Biosciences, Hyderabad, India. HPLC purity of the synthesized compound was estimated to be >95% purity and >98% ee. Data from the $^{1}H$ NMR (400 MHz, CDCl$_3$) and mass spectrometry analyses were in agreement with the literature. DPOFA was prepared according to the method described in Scheme 1.

Scheme 1

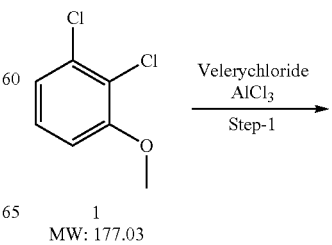

1
MW: 177.03

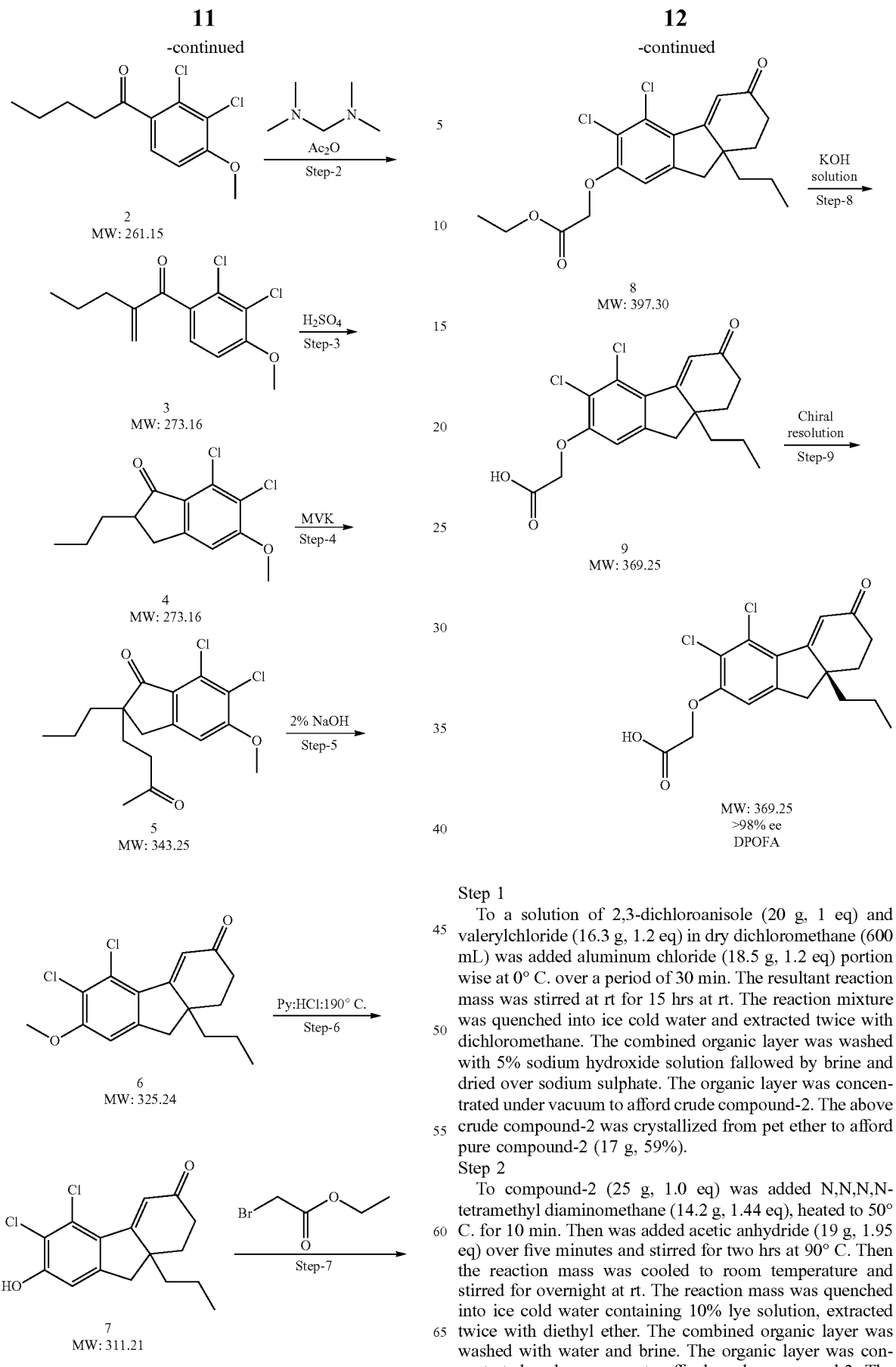

Step 1

To a solution of 2,3-dichloroanisole (20 g, 1 eq) and valerylchloride (16.3 g, 1.2 eq) in dry dichloromethane (600 mL) was added aluminum chloride (18.5 g, 1.2 eq) portion wise at 0° C. over a period of 30 min. The resultant reaction mass was stirred at rt for 15 hrs at rt. The reaction mixture was quenched into ice cold water and extracted twice with dichloromethane. The combined organic layer was washed with 5% sodium hydroxide solution fallowed by brine and dried over sodium sulphate. The organic layer was concentrated under vacuum to afford crude compound-2. The above crude compound-2 was crystallized from pet ether to afford pure compound-2 (17 g, 59%).

Step 2

To compound-2 (25 g, 1.0 eq) was added N,N,N,N-tetramethyl diaminomethane (14.2 g, 1.44 eq), heated to 50° C. for 10 min. Then was added acetic anhydride (19 g, 1.95 eq) over five minutes and stirred for two hrs at 90° C. Then the reaction mass was cooled to room temperature and stirred for overnight at rt. The reaction mass was quenched into ice cold water containing 10% lye solution, extracted twice with diethyl ether. The combined organic layer was washed with water and brine. The organic layer was concentrated under vacuum to afford crude compound-3. The above crude compound-3 was crystallized from pet ether to afford pure compound-3 (20 g, 76%).
Step 3
To sulphuric acid (90 ml) was added compound-3 (20 g) in portions wise at room temperature and stirred for overnight at room temperature. The reaction mass was quenched into ice cold water, and stirred for 1 hrs. The resultant solid was filtered and washed with water and dried to afford almost pure compound-4 (14 g). The above compound-4 was taken into the next step without further purification.
Steps 4-5
To a solution of compound-4 (10 g, 1.0 eq) in methanol (300 mL) was added 2% potassium hydroxide solution (20 mL). The resultant solution was stirred for 15 minutes at RT. Then methyl vinyl ketone (2.56 g, 1 eq) was added drop wise in 5 min, stirred for 30 min at RT. Then the reaction mixture was heated to reflux for overnight. The reaction mass was concentrated under vacuum and added water, and adjusted the pH to 3-4 with 1 N HCl. Then the aq layer was extracted twice with DCM. The combined organic layer was washed with water and brine, dried over sodium sulphate and concentrated under vacuum to afford crude compound-6. The crude compound-6 was purified on silica gel column (100-200 mesh) using 20-25% ethyl acetate in pet ether as eluent (4.5 g, 38%).
Step 6
Compound-6 (5 g, 1.0 eq) and pyridine hydrochloride (40 g, 24 eq) was taken into a microwave vial and heated at 200° C. for 10 min. The reaction mass was poured into ice cold water and stirred for 10 min. Filtered the obtained solid and washed with water and dried to get crude compound-7. The above solid was purified on column of silica gel (100-200 mesh) using 1-2% methanol in dichloromethane as eluent (2.9 g, 60%).
Step 7
Compound-7 (7 g, 1.0 eq) ethyl bromo acetate (5.3 g, 1.4 eq) and potassium carbonate (9.3 g, 3.0 eq) in acetonitrile (40 mL) was taken in microwave vial and heated at 110° C. for 20 min. The reaction mass was diluted with water and extracted twice with ethyl acetate. The combined organic layer was washed with water and brine. The organic layer was concentrated under vacuum to afford crude compound-8. The crude compound-8 was purified on silica gel column (100-200 mesh) using 0.5 to 1% methanol in dichloromethane as eluent (3.4 g, 38%).
Step 8
To compound-8 (5 g) in ethanol (50 mL) was added potassium hydroxide solution (22 mL) and the resultant solution was stirred overnight at rt. The reaction mass was concentrated under vacuum and added water. The aqueous reaction mass was adjusted pH to 2 with 2N HCl, filtered the resultant solid and washed with water and dried to get crude compound-9 as racemic mixture. The crude compound-9 was purified as a racemic mixture on silica gel column (100-200 mesh) using 2-3% methanol in dichloromethane as eluent (2 g, 44%).
Step 9
Compound-9 (98% ee) was resolved by chiral column chromatography (Column: CHIRAL PAK 1A, 4.6×250 mm, 5 μm; Mobile phase: A: n-Hexane (0.1% TFA), B: Ethanol, C: DCM; Isocratic: 35:2:63; Flow rate: 1.0 ml/min; Diluent: DCM).

Example 2. DPOFA Lowers Serum Uric Acid Levels

DPOFA was originally studied for treating brain edema but failed to cross the blood-brain barrier in humans. It was discovered that systemic intraperitoneal administration of DPOFA in guinea pigs induced a pronounced reduction in serum uric acid (FIG. 1). The maximum reduction of uric acid in guinea pigs was seen at the 7 hour time point following systemic administration of DPOFA of 20 mg (FIG. 1).

Example 3. DPOFA Lowers Serum Uric Acid Levels in Subjects with Gout

An amount of compound DPOFA is administered to a human subject afflicted with gout. The amount of the compound is effective to treat the subject afflicted with gout. The compound reduces serum uric acid levels in the subject by increasing renal clearance of uric acid. The amount of the reduction in serum uric acid levels is effective to treat the gout in the subject.

Example 4. DPOFA in Combination with XO Inhibitor

An amount of compound DPOFA in combination with allopurinol or febuxostat is administered to a subject afflicted with gout. The amount of the compound and allopurinol or febuxostat is effective to treat the subject afflicted with gout. The combination is more effective in treating the gout than each compound administered alone.

Example 5. DPOFA Prevents Gout in Subjects

An amount of compound DPOFA is administered to a subject with a history of gout flares or who is at risk for a gout flare. The amount of the compound is effective to prevent gout flares in the subject. The compound reduces serum uric acid levels or maintains normal serum uric acid levels in the subject by increasing renal clearance of uric acid. The amount of the reduction or maintenance of serum uric acid levels is effective to prevent gout in the subject.

Example 6. DPOFA in Combination with XO Inhibitor Prevents Gout in Subjects

An amount of compound DPOFA in combination with allopurinol or febuxostat is administered to a subject with history of gout flares or who is at risk for a gout flare. The amount of the compound and allopurinol or febuxostat is effective to prevent gout flares in the subject. The combination is more effective in preventing the gout than each compound administered alone.

DISCUSSION

The present invention relates to a fluorenone compound for treatment of gout. Disclosed herein is a fluorenone compound which has a mechanism of action distinct from the current therapies for treating gout. Wherein xanthine oxidase inhibitors are effective in lowering uric acid levels by reducing the production of uric acid, the fluorenone compound described herein increases renal clearance of the uric acid. Since elevated levels of circulating uric acid most commonly result from undersecretion of uric acid in the kidneys as opposed to overproduction of xanthine oxidase, the method contained herein are is more effective to lower uric acid levels and treat gout.

The fluorenone DPOFA, (R)-(+)-(5,6-dichloro-2,3,9,9a-tetrahydro-3-oxo-9a-propyl-1H-fluoren-7-yl)oxy]acetic acid, was originally developed for trauma-induced brain damage. As described herein, DPOFA reduced uric acid levels in the blood of a guinea pig and increases uric acid levels in the urine, indicating that DPOFA increases renal clearance of uric acid and is useful for the treatment of gout.

Probenecid is a urate-lowering therapy (ULT) in patients with gout where xanthine oxidase inhibitors are ineffective, not tolerated, or contraindicated. Probenecid is believed to interfere with the kidneys' organic anion transporter (OAT), which reclaims uric acid from the urine and returns it to the plasma, thereby preventing reabsorption of the uric acid. However, in one study, target serum urate concentrations (<0.36 mmol/l) were achieved in 10/30 (33%) of the probenecid monotherapy group and 10/27 (37%) of the allopurinol combination treatment group (Pui, K. et al. 2013). Adverse effects were also seen in 19% of subjects tested (Pui, K. et al. 2013).

DPOFA is more effective than probenecid at lowering serum urate levels and increasing excretion of uric acid with reduced side effects. Lesinurad, a compound being developed by AstraZeneca, is a selective uric acid re-absorption inhibitor (SURI). Clinical trials have demonstrated that lesinurad (400 mg), in combination with febuxostat, lowers serum uric acid greater than febuxostat alone in patients who had at least one measurable tophus (76% of patients meeting target serum levels relative to 46%). However, at the 200 mg dose, lesinurad failed to show a significant improvement at six months, the primary endpoint in the trial (McKee, S. 2015). This result is noteworthy because of potential kidney toxicity at the higher dose. Treatment with lesinurad coincided with a rise in serum creatinine levels and higher rate of renal-related AEs (particularly in the 400 mg group). Further, the combination did not result in a significant difference in the proportion of subjects achieving a complete resolution of at least one tophus by month 12.

DPOFA is more effective than leisured at lowering serum urate levels and increasing excretion of uric acid with reduced side effects.

REFERENCES

Burns C, et al. (2013) CURRENT Rheumatology Diagnosis & Treatment, 3e. New York, N.Y.: McGraw-Hill.

Choi H K, Atkinson K, Karlson E W, Curhan G. (2005) Obesity, weight change, hypertension, diuretic use, and risk of gout in men. Arch Intern Med. 165, 742-748.

Choi H K, Atkinson K, Karlson E W, Willet W, Curhan G. (2004a) Alcohol intake and risk of incident gout in men: a prospective study. Lancet. 363, 1277-12781.

Choi H K, Atkinson K, Karlson E W, Willet W, Curhan G. (2004b) Purine-rich foods, dairy and protein intake, and the risk of gout in men. N Engl J Med. 350,1093-1103.

Hsyu P H, Gisclon L G, Hui A C, Giacomini K M (1988). "Interactions of organic anions with the organic cation transporter in renal BBMV". Am. J. Physiol. 254 (1 Pt 2), F56-61.

Krishnan E. (2013) Chronic kidney disease and the risk of incident gout among middle-aged men. Arthritis Rheum. 65(12), 3271-3278.

Lawrence R. C., Felson D. T., Helmick C. G., Arnold L. M., Choi H., Deyo R. A., et al. Estimates of the prevalence of arthritis and other rheumatic conditions in the United States. Part II. Arthritis Rheum. 2008; 58: 26-35.

Love B L, Barrons R, Veverka A, Snider K M (2010). "Urate-lowering therapy for gout: focus on febuxostat". Pharmacotherapy 30 (6): 594-608.

McKee, S. "Higher dose of AZ' gout drug hits PhIII goals" PharmaTimes Digital, Jun. 14, 2015.

Pui, K. et al. (2013) "Efficacy and tolerability of probenecid as urate-lowering therapy in gout; clinical experience in high-prevalence population" J. Rheumatol. 40(6), 872-6.

Shen Z et al. (2015) Pharmacokinetics, pharmacodynamics, and safety of lesinurad, a selective uric acid reabsorption inhibitor, in healthy adult males. Drug Des Devel Ther. 9, 3423-34.

Stamp L K, Chapman P T, Palmer S C. (2015) Allopurinol and kidney function: An update. Joint Bone Spine. pii: S1297-319X(15)00164-5

Terkeltaub, R A. (2001) Gout: epidemiology, pathology and pathogenesis. In: J. H. Klippel, L. J. Crofford, J. H. Stone, C. D. Weyand (Eds.) Primer on the Rheumatic Diseases. 12th ed. Arthritis Foundation, Atlanta, Ga., 307-312.

What is claimed is:

1. A method for treating or preventing gout in a subject comprising administering to the subject an effective amount of a compound having the structure:

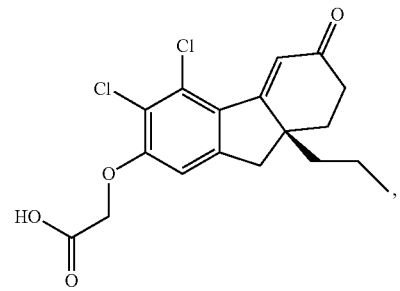 [SMILES: CCC[C@]12CCC(=O)C=C1c1c(cc(OCC(=O)O)c(Cl)c1Cl)C2]

or an ethyl ester or salt thereof, so as to thereby treat or prevent the gout in the subject.

2. The method of claim 1, wherein the compound treats gout in the subject.

3. The method of claim 2, wherein the treating comprises increasing uric acid levels in the urine of the subject.

4. The method of claim 2, wherein the treating comprises reducing uric acid levels in the blood of the subject.

5. The method of claim 2, wherein the treating comprises increasing uric acid clearance in the subject; or the treating comprises decreasing uric acid reabsorption in the kidneys of the subject; or the treating comprises increasing renal clearance of uric acid in the subject.

6. The method of claim 2, wherein the treating comprises reducing one or more symptoms associated with gout in the subject.

7. The method of claim 6, wherein the one or more symptoms associated with gout are joint pain, joint inflammation, joint redness, decreased range of motion at the joint.

8. The method of claim 1, wherein the compound prevents gout in the subject.

9. The method of claim 8, wherein the preventing comprises increasing uric acid levels in the urine of the subject; or the preventing comprises reducing uric acid levels in the blood of the subject; or the preventing comprises increasing uric acid clearance in the subject; or the preventing comprises decreasing uric acid reabsorption in the kidneys of the subject; or the preventing comprises increasing renal clearance of uric acid in the subject.

10. The method of claim 2, wherein the gout is chronic gout or acute gout.

11. The method of claim 8, wherein acute gout or a recurrence of chronic gout is prevented.

12. The method of claim 1, further comprising administering to the subject a xanthine oxidase inhibitor.

13. The method of claim 12, wherein the xanthine oxidase inhibitor is allopurinol, febuxostat, oxypurinol, tisopurine, inositol, phytic acid, myo-inositiol, kaempferol, myricetin or quercetin.

14. The method of claim 1, wherein the subject is a mammal.

15. The method of claim 1, wherein the subject is female and administration of the compound reduces the uric acid level to 2.4-6.0 mg/dL.

16. The method of claim 1, wherein the subject is male and administration of the compound reduces the uric acid level to 3.4-7.0 mg/dL.

17. The method of claim 1, wherein the administration of the compound reduces uric acid levels in the subject to less than 7 mg/dL.

18. A method for treating or preventing hyperuricemia in a subject afflicted therewith comprising administering a compound having the structure:

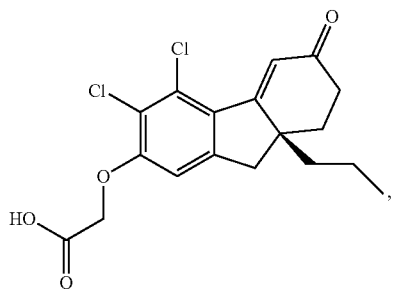 [SMILES: CCC[C@]12CCC(=O)C=C1c1c(cc(OCC(=O)O)c(Cl)c1Cl)C2]

or an ethyl ester or salt thereof, so as to thereby treat or prevent the hyperuricemia in the subject.

19. The method of claim 1, wherein the compound has the structure:

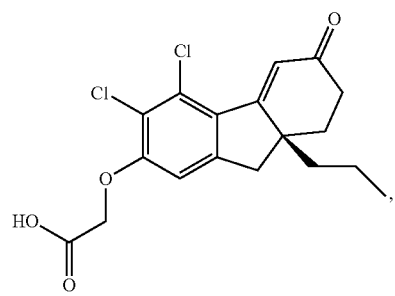 [SMILES: CCC[C@]12CCC(=O)C=C1c1c(cc(OCC(=O)O)c(Cl)c1Cl)C2]

or a salt thereof.

20. The method of claim 18, wherein the compound has the structure:

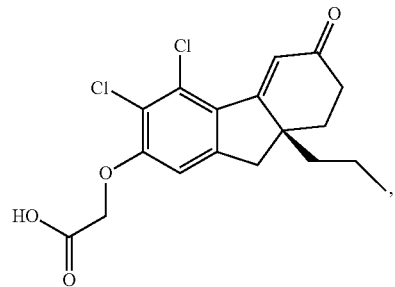 [SMILES: CCC[C@]12CCC(=O)C=C1c1c(cc(OCC(=O)O)c(Cl)c1Cl)C2]

or a salt thereof.

* * * * *